United States Patent [19]

Imagawa et al.

[11] Patent Number: 4,470,414
[45] Date of Patent: Sep. 11, 1984

[54] LASER SURGICAL KNIFE

[75] Inventors: Kyoshiro Imagawa; Tomoyuki Haga, both of Kyoto, Japan

[73] Assignee: Agency of Industrial Science & Technology, Tokyo, Japan

[21] Appl. No.: 313,196

[22] Filed: Oct. 20, 1981

[30] Foreign Application Priority Data

Nov. 4, 1980 [JP] Japan .............................. 55-153736

[51] Int. Cl.³ .............................................. A61B 17/36
[52] U.S. Cl. .......................... 128/303.1; 219/121 LA
[58] Field of Search .................. 128/303.1, 395–398; 219/121 LB, 121 LA

[56] References Cited

U.S. PATENT DOCUMENTS 3,843,865  10/1974  Nath ................................ 128/395 X
4,126,136  11/1978  Auth et al. ........................ 128/303.1
4,232,678  11/1980  Skovajsa ............................ 128/395
4,316,467  2/1982   Muckerheide ..................... 128/303.1

FOREIGN PATENT DOCUMENTS 2145921  3/1973  Fed. Rep. of Germany ... 128/303.1
2829516  1/1980  Fed. Rep. of Germany ... 128/303.1

Primary Examiner—Lee S. Cohen
Attorney, Agent, or Firm—Wenderoth, Lind & Ponack

[57] ABSTRACT

A laser surgical knife characterized by switches, which can adjust an output power within the safe scope from the output power preliminarily set for a laser oscillator, mounted on an attachment of said laser surgical knife which is held by an operating surgeon's hand in order to irradiate laser rays on the affected parts.

The present invention can provide a laser surgical knife of which output power can be changed at one touch and in safe without interrupting surgical operations merely by a simple process in which an operating surgeon operates a handy switch for himself.

3 Claims, 3 Drawing Figures

LASER SURGICAL KNIFE

BACKGROUND OF THE INVENTION

1. Field of the Invention

The present invention relates to a laser surgical knife developed for operating upon an affected part, taking advantage of the cutting effect and the bleeding-stopping effect of laser generated rays.

2. Description of the Prior Art

In surgical operations using a laser surgical knife of this type, the output power of the laser rays used is dependent upon the kind of surgical operation, the depth of the affected part to be cut and the like. Consequently, it is usual to begin surgical operations after preliminarily adjusting the output power of a laser oscillator to the desired extent by manipulating a control apparatus of said laser oscillator. However, sometimes we meet with surgical operations in which it is necessary to change the output power. In such cases, at present, the output power of a laser oscillator is changed in such a manner that an operating surgeon turns a power supply off by means of a foot switch and the like and then either an operating surgeon or a nurse or the like operates the control apparatus. Safety is the reason for the power supply being turned off when the output power is changed. The above described manner has a disadvantage that the surgical operation time is prolonged because the surgical operation must be interrupted every time the output power is changed. In addition, the change in the output power must be regulated in a small range corresponding to only a small percentage of the normal output power. Accordingly, sometimes an excessive output power is generated due to the inexperience of an operating surgeon or nurse in the handling of the control apparatus or their misoperations. This exposes a patient to great danger.

SUMMARY OF THE INVENTION

The present invention provides a laser surgical knife whose output power can be safely changed by a single touch without interrupting surgical operations merely by a simple process in which an operating surgeon personally operates a handy switch.

BRIEF DESCRIPTION OF THE DRAWINGS

The drawings show examples of the present invention, in which.

DESCRIPTION OF THE PREFERRED EMBODIMENTS

Figure 1:
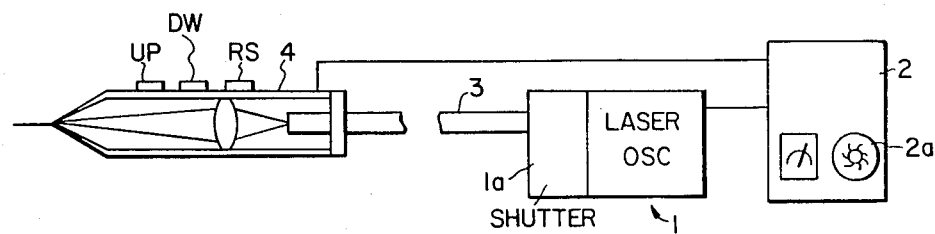
FIG. 1 is a diagram showing a laser surgical knife as one example of the present invention.

The construction of a laser surgical knife according to the present invention will be described below by reference to the drawings. FIG. 1 shows one example of a laser surgical knife according to the present invention where element 1 is a laser oscillator provided with a shutter 1a at an exit of laser rays; element 2 is a control apparatus which can change the output power of said oscillator 1, the apparatus being able to keep said shutter 1a in the open mode (opened state) or the closed mode (closed state), and at the same time being able to set the output power of said laser oscillator to be controlled; element 3 are fiber optics for transmitting laser rays; element 4 is an attached laser surgical knife, which can be held by an operating surgeon's hand, for applying laser rays transmitted through said fiber optics 3 to the affected parts. The knife attachment 4 is provided with a reset switch RS, a power-down switch DW and a power-up switch UP which protrude at places on the surface thereof which are easy to push and handle. Each of said switches is electrically connected to said laser oscillator 1 through said control apparatus 2. Said switch RS can turn said shutter 1a to its closed mode by its off-operation and turn said shutter 1a to its open mode by its on-operation. When said shutter 1a is turned to its open mode, laser rays having the output power preliminarily set in said laser oscillator 1 (hereinafter referred to as the output power in the normal mode) are irradiated through said laser surgical knife attachment 4. In addition, from a viewpoint of safety in surgical operations, said laser oscillator 1 is constructed so as not to be activated unless said switch RS is in off-position.

Said output power in the normal mode can be decreased by pushing said switch DW and increased by pushing said switch UP. The range, in which said output power of normal mode is decreased or increased by means of these switches, is selected so as to be within the range, in which the safety of surgical operations can be secured; that is to say, the range in which the safety of surgical operations can be secured even though said switches are pushed by mistake. It is desired that such a range is generally from the output power in the normal mode+10% to the output power in the normal mode—10%. However, the range of the output power is dependent upon the magnitude of the output power in the normal mode. For example, it is necessary to select a still narrower range when the output power in the normal mode is large and it changes by several tens watts even though it is only changed by a few percent while sometimes it is necessary to select a still wider range of 50% or 100% when the output power in the normal mode is small and it cannot be changed to the extent which is necessary and effective for carrying out surgical operations with a change of only about 10%. It is desired to arrange a micro power adjusting dial 2a on the front of said control apparatus 2 and make it possible to change the range in which the output power is decreased or increased by turning said dial 2a. The ratio of the range in which the output power is decreased or increased with respect to the output power in the normal mode may be graduated in % on said dial 2a or the range in which the output power is decreased or increased may be graduated in watts on said dial 2a.

Figure 2:
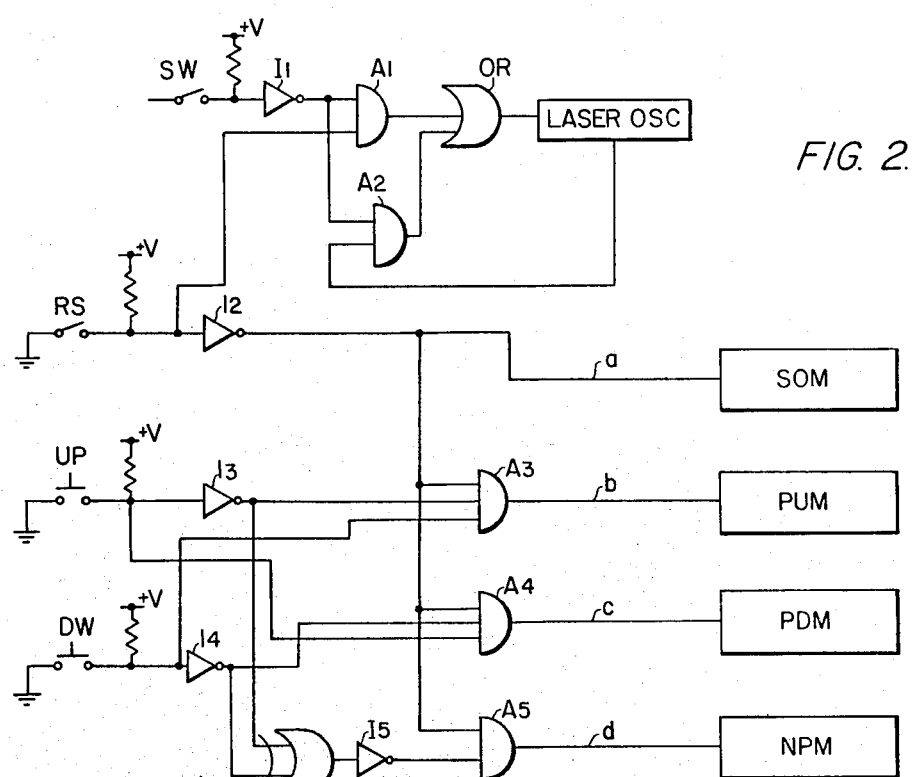
FIG. 2 is a circuit diagram of an electrical circuit governing the action of the main parts of a laser surgical knife shown in FIG. 1.

How an output power is increased or decreased by means of said switch DW and said switch UP can be decided depending upon an electric circuit included in said control apparatus 2. FIG. 2 shows an example of electric circuits generating signals for decreasing or increasing the output power by means of said switch DW and said switch UP. Referring to FIG. 2, SOM (shutter-open mode), PUM (power-up mode), PDM (power-down mode) and NPM (normal power mode) mean that they are turned to such modes (states) when a signal from signal lines a, b, c, d, which are connected to each of them, is respectively turned to a high level. Such modes can be achieved by the process in which said control apparatus 2 receives a signal from each of said signal lines a, b, c, d and said laser oscillator 1 is automatically controlled on the basis of said signal. In addition, SW designates a switch for activating said laser oscillator 1; elements $I_1$ to $I_5$ are invertors; elements $A_1$ to $A_5$ are AND circuits; elements OR is an OR circuit; element EX is an exclusive OR circuit. Said exclusive OR circuit provides a low level output when both of its two inputs are at a high level or at a low level and provides a high level output when one of its two inputs is at a high level and the other input is at a low level.

Referring to FIG. 2, said laser oscillator 1 is activated when said switch SW is pushed, provided that said switch RS is in its off-position. Once said laser oscillator 1 is activated, it continues to oscillate whether said switch RS is in its on-position or in its off-position as long as said switch SW is in on-position. While said laser oscillator 1 is in an activated state, signals from said signal lines a, d are turned to a high level when said switch RS is turned "ON" and said shutter 1a is opened, thereby enabling the output power in the normal mode to be irradiated through said laser surgical knife attachment 4. In this time, a signal from said signal line b is turned to a high level and a signal from said signal line d is turned to a low level when said switch UP is pushed. Accordingly, the output power irradiated through said laser knife attachment 4 is increased. The amount of this increase is dependent upon the above described set value of said micro adjusting dial 2a. On the other hand, a signal from said signal line c is turned to a high level and a signal from said signal line d is turned to a low level when said switch DW is pushed. Accordingly, the output power irradiated through said laser surgical knife attachement 4 becomes lower than that in the normal mode. The amount of this decrease is also dependent upon the above described set value of said micro adjusting dial 2a. In addition, in case both said switch UP and said switch DW are pushed by mistake, both of said signal lines b, c are turned to a low level and a signal from said signal line d is turned to a high level. Accordingly, the output power irradiated through said knife attachment 4 is held at the same level as that in the normal mode.

The use of a laser surgical knife having the above described construction makes possible the change of the output power during surgical operations at one touch without the help of others such as nurses and the like by a simple process in which an operating surgeon personally pushes said switch DW or said switch UP mounted on said knife attachment 4. Accordingly, surgical operations can be carried out without interruptions and they can thereby be finished within a shorter time. In addition, although the change of the output power is left to the operating surgeon's care, the change of the output power is done merely within the range in which the safety of surgical operations is secured; thus, there are no danger even though an operating surgeon pushes said switch UP instead of said switch DW by mistake.

Figure 3:
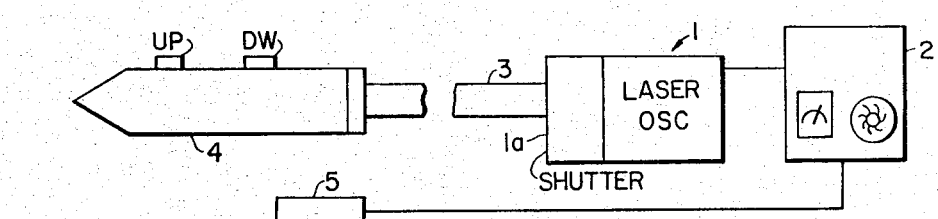
FIG. 3 is a diagram showing another example of the present invention.

Although said laser surgical knife attachment is also provided with said switch RS in the above described construction, this switch can be replaced by a foot switch 5, for example, as shown in FIG. 3. Said foot switch 5 may be used together with said switch RS.

Furthermore, in case it is necessary to change the output power in still more steps, for example, in three stages within the preliminarily set adjusting range it is only necessary to construct said control circuit so as to be adjusted on the basis of the number of times said switch DW and said switch UP are pushed and to install a pilot lamp and the like separately.

As described above, a laser surgical knife according to the present invention has a construction in which a laser oscillator is provided with switches on a laser surgical knife attachment which can adjust the output power within a safe range from the output power preliminarily set for said laser oscillator. Consequently, the following effects can be attained:

(a) A laser surgical knife according to the present invention is remarkably easy to handle because the output power can be adjusted by operating switches mounted on an attachment of the laser surgical knife and consequently, an operating surgeon can easily change an output power for himself, if the need arises, without the help of others such as nurses and the like.

(b) There is not the slightest fear that misoperations interfere with surgical operations because the range in which the output power is changed by means of the switches is limited to a safe range. That is to say, the safety of surgical operations is always secured even though an operating surgeon gives rise to misoperations by mistake.

(c) It is not necessary to turn off the power supply every time the output power is changed because the output power can be changed within a safe range by means of a handy switch. Consequently, an operating surgeon can carry out surgical operations without interruptions within a shorter time, changing the output power for himself if the need arises.

What is claimed is:

1. A laser surgical knife comprising:
   a laser oscillator for outputting laser rays;
   an attachment means of said laser surgical knife which is held by an operating surgeon's hand for irradiating laser rays from said laser oscillator on an affected operation area;
   a manually operated adjusting means electrically connected to said laser oscillator for adjusting its output power, said adjusting means including a plurality of manually operated switches which are mounted on said attachment means of said laser surgical knife;
   a laser beam outlet shutter means operatively connected to and controlled by one of said plurality of manually operated switches, said shutter means having an open position for passing said beam to said attachment means and a closed position for preventing passage of said beam to said attachment means;
   wherein said adjusting means includes a control means for permitting the activation of said oscillator only when said shutter means is closed and for permitting changes in said output power of said laser oscillator by the manual operation of said plurality of manually operated switches only relative to a preset normal mode output power and within preset safe operating limits.

2. A laser surgical knife as recited in claim 1, wherein said attachment means has said plurality of switches contained therein, said plurality of switches including a switch for operating said shutter means, a power-up switch and a power-down switch for respectively increasing and decreasing said output power of said laser oscillator, and wherein said control means is arranged such that if both said power-up and power-down switches are simultaneously operated, then said output power of said laser oscillator is kept at said preset normal mode power output.

3. A laser surgical knife as recited in claim 2, including a first inverter, wherein said switch for operating said shutter means is operatively connected to said shutter means by said first inverter and wherein said manually operated adjusting means includes a power-up means and a power-down means for respectively increasing and decreasing said output power of said laser oscillator in response to said power-up and power-down switches and a normal power means for setting said power output of said laser oscillator at its preset normal mode output power;

and a first three-input AND gate and a second inverter, wherein said power-up means has an output of said three-input AND gate connected to its input, one input of said and gate being connected to an output of said first inverter and another input of which is connected to said power-up switch through said second inverter and another input of which is connected to said power-down switch;

and a second three-input AND gate and a third inverter, wherein said power-down means has an output of said second three-input AND gate connected to its input, one input of said second AND gate being connected to said output of said first inverter and another input of which is connected to said power-up switch and another input of which is connected to said power-down switch through said third inverter;

and a two-input AND gate, a fourth inverter and a two-input exclusive OR gate, wherein said normal power means has an output of said two-input AND gate connected to its input, one input of said two-input AND gate being connected to said output of said first inverter and the other input of which is connected to an output of said fourth inverter whose input is connected an output of said two-input exclusive-OR gate whose inputs are respectively connected to the outputs of said second inverter and said third inverter.

* * * * *